United States Patent [19]

Takagi et al.

[11] Patent Number: 4,598,066
[45] Date of Patent: Jul. 1, 1986

[54] ANTIMYCOPLASMAL AGENT FOR ANIMALS AND METHOD OF USE FOR PREVENTION AND TREATMENT OF MYCOPLASMOSIS

[75] Inventors: Hirofumi Takagi; Kiyohiko Kunugita; Hideki Sawai, all of Sakura; Kazuo Kariyone, Kyoto, all of Japan

[73] Assignee: Fujisawa Pharmaceutical Co., Ltd., Osaka, Japan

[21] Appl. No.: 535,332

[22] Filed: Sep. 23, 1983

[30] Foreign Application Priority Data

Oct. 11, 1982 [GB] United Kingdom ............... 8228988

[51] Int. Cl.$^4$ .......................... C07K 5/06; C07K 7/02
[52] U.S. Cl. ......................................... 514/18; 514/19
[58] Field of Search .......................... 424/177; 514/19

[56] References Cited

U.S. PATENT DOCUMENTS 4,070,458  1/1978  Umezawa et al. ................. 424/177
4,322,341  3/1982  Kitaura et al. ..................... 424/177
4,399,066  8/1983  Nakaguchi et al. ........... 260/112.5 R

OTHER PUBLICATIONS

Stedman's Medical Dictionary, 23rd Ed., The Williams & Wilkins Company, Baltimore, pp. 911 and 1040.

*Primary Examiner*—Delbert R. Phillips
*Assistant Examiner*—F. T. Moezie
*Attorney, Agent, or Firm*—Oblon, Fisher, Spivak, McClelland & Maier

[57] ABSTRACT

The invention relates to an antimycoplasmal agent for prevention or treatment of mycoplasmosis in animals comprising an acyl peptide of the formula

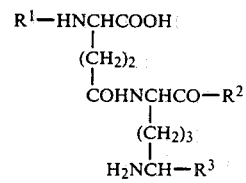

wherein
 $R^1$ is lactoyl-alanyl, $R^2$ is carboxymethylamino and $R^3$ is carboxy; or
 $R^1$ is heptanoyl, $R^2$ is 1-carboxyethylamino and $R^3$ is carboxy; or
 $R^1$ is stearoyl, $R^2$ is 1-carboxyethylamino and $R^3$ is hydrogen, or its non-toxic salt, optionally in combination with an antibotic.

6 Claims, No Drawings

ANTIMYCOPLASMAL AGENT FOR ANIMALS AND METHOD OF USE FOR PREVENTION AND TREATMENT OF MYCOPLASMOSIS

This invention relates to a new antimycoplasmal agent for animals. More particularly, it relates to a new antimycoplasmal agent for animal which comprises an acyl peptide or its non-toxic salt as an effective ingredient, and to methods of use of the acyl peptide or its non-toxic salt for prevention and treatment of mycoplasmosis of animals.

The acyl peptide to be used in this invention is represented by the following formula (I):

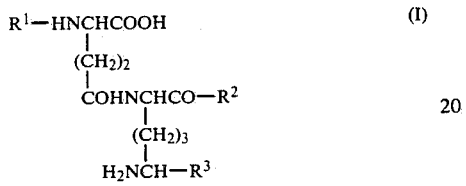

wherein
$R^1$ is lactoyl-alanyl, $R^2$ is carboxymethylamino, and $R^3$ is carboxy; or
$R^1$ is heptanoyl, $R^2$ is 1-carboxyethylamino and $R^3$ is carboxy; or
$R^1$ is stearoyl, $R^2$ is 1-carboxyethylamino and $R^3$ is hydrogen.

The acyl peptide (I) and its non-toxic salt to be used in this invention is the known one possessing an enhancing activity of immune response [cf. U.S. Pat. No. 4322341].

Some antibiotics have been used as an antimycoplasmal agent for animal, including, for example, tylosin, tetracyclines, chloramphenicol, tiamulin, spectinomycin and the like. These antibiotics used as an antimycoplasmal agent for animals are characterized by their strong antimicrobial activities.

However, the antimycoplasmal agent for animal comprising such antibiotics on market can not be said to be entirely sufficient in the actual application thereof to animals due to the problems of occurrence of antibiotic resistant microorganisms and so on.

The acyl peptide (I) is inactive against microorganisms in vitro, although it possesses an enhancing activity of immune response and protective efficacy in experimental infection.

Accordingly, if the acyl peptide (I) possessing such unique pharmacological properties can effectively be used as an antimycoplasmal agent for animal, an actually useful antimycoplasmal agent which is not accompanied with occurrence of antibiotic-resistant microorganisms, can be provided.

On the basis of these factual situations, the inventors of this invention have studied a possibility of the effective use of the acyl peptide (I) for prevention and treatment of mycoplasmosis of animal. And the extensive studies of the inventors have successfully resulted in providing a new antimycoplasmal agent for animal comprising the acyl peptide (I) or its non-toxic salt.

Accordingly, this invention provides a new antimycoplasmal agent comprising the acyl peptide (I) or its non-toxic salt as an effective ingredient and method of use of the acyl peptide (I) or its non-toxic salt for prevention and treatment of mycoplasmosis of animals.

A non-toxic salt of the acyl peptide (I) may include a salt with an inorganic or organic base such as a sodium salt, potassium salt, calcium salt, ammonium salt, ethanolamine salt, triethylamine salt, dicyclohexylamine salt and the like, and an acid addition salt with an organic or inorganic acid such as acetate, trifluoroacetate, lactate, maleate, fumarate, tartrate, citrate, methane sulfonate, hydrochloride, sulfate, nitrate, phosphate and the like.

As to the acyl peptide (I) to be used in this invention, it is to be noted that said acyl peptide includes one or more stereoisomers due to the asymmetric carbon atoms in the molecule, and all of such isomers are included within the scope of the active ingredient of this invention.

Representative compounds of the acyl peptide (I) to be used in this invention are as follows:

Compound 1:

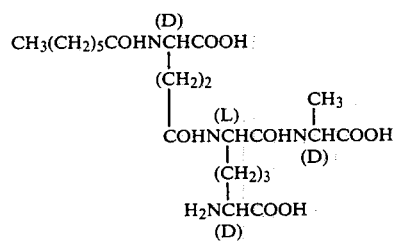

Compound 2:

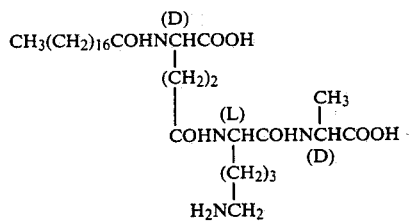

Compound 3:

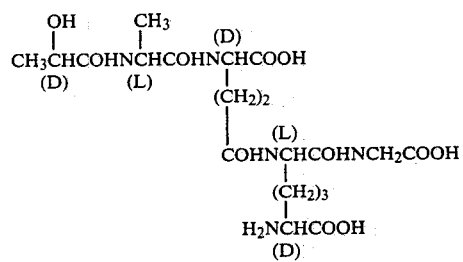

The antimycoplasmal agent of this invention which comprises the acyl peptide (I) or its non-toxic salt as an effective ingredient, is administered to animals in a conventional manner. Namely, the antimycoplasmal agent of this invention is preferably administered orally to animals, and the effective ingredient, the acyl peptide (I) or its non-toxic salt may be generally administered as it is or in admixture with a suitable carrier (e.g. water, etc.) or in admixture with an animal nutrition source, i.e. feed. More particularly, the effective ingredient, the acyl peptide (I) or its non-toxic salt may be administered to as a drinking water in the form of aqueous solution, or as a ration in the form of the composition which comprises the acyl peptide (I) or its non-toxic salt and animal feed and sometimes the other feed additive.

In connection with the form of administering the animal feed composition of this invention as mentioned above, the ration comprising the acyl peptide (I) or its non-toxic salt can be prepared in a conventional manner; namely, by admixing the acyl peptide (I) or its non-toxic salt with basal ration. And, as the basal ration, natural feed and assorted feed can be used, including dry feeds, liquid feed, pelleted feed and the like. As preferred basal ration, there is preferably used the assorted feed which comprises one or more conventional feeds such as corn, rice, wheat, milo, soybean meal, cottonseed meal, wheat bran, defatted rice bran, fish meal, skim milk, dried whey, oils, fats, alfalfa meal or the like and one or more of the conventional feed additives such as tricalcium carbonate, sodium chloride, choline chloride, vitamin (e.g. vitamin A, vitamin D, vitamin E, vitamin $B_1$, vitamin $B_2$, vitamin $B_6$, vitamin $B_{12}$, calcium pantothenate, nicotinamide, folic acid, etc.), amino acid (e.g. lysine, methionine, etc.), mineral source (e.g. magnesium sulfate, ferrous sulfate, copper sulfate, zinc sulfate, potassium iodide, cobalt sulfate, etc.) or the like.

The amounts of the acyl peptide (I) or its non-toxic salt in the basal rations which are fed to the animals may be varied over a very wide range depending upon the kind, growth period, etc. of the animals and the severity of mycoplasmosis of animal and the like. Preferred levels are in an amount between about 0.01 p.p.m. and about 100 p.p.m, more preferably between about 0.1 p.p.m. and about 40 p.p.m.

The antimycoplasmal agent of this invention may also be administered non-orally to animals, such as intravenous, intramuscular, intraperitoneal or subcutaneous injection, spray or the like. In such a non-oral administration, the effective ingredient, the acyl peptide (I) or its non-toxic salt may be preferably administered in admixture with a suitable carrier such as water or the like.

Dosage of the antimycoplasmal agent to animals is varied depending upon the kind, the severity of mycoplasmosis, etc. of the animals, and its preferred dosage may usually be selected from the range of about 0.01–10 mg/kg/day as the amount of the acyl peptide (I) or its non-toxic salt.

The antimycoplasmal agent for animal of this invention may be used for both of prevention and treatment of mycoplasmosis of animals, and preferably used for prevention of mycoplasmosis of animals.

As described above, the effective ingredient, the acyl peptide (I) or its non-toxic salt itself, of antimycoplasmal agent for animal of this invention is effective for prevention and treatment of mycoplasmosis of animals.

In addition to this, it has been newly found the acyl peptide (I) or its non-toxic salt exhibits a synergistic antimycoplasmal activity by combining some antibiotics such as tylosin, tetracyclines, chloramphenicol, tiamulin, spectinomycin or the like (hereinafter referred to the antibiotics).

Accordingly, the antimycoplasmal agent of this invention may be also used as the one comprising as an effective ingredient the acyl peptide (I) or its non-toxic salt and the antibiotics or their non-toxic salt for prevention and treatment of mycoplasmosis of animal.

As preferred examples of the non-toxic salt of the present antibiotics, there may be exemplified the same as those exemplified for the acyl peptide (I).

When the effective ingredient of the antimycoplasmal agent of this invention is used in a combination of the acyl peptide (I) or its non-toxic salt and the antibiotics or their non-toxic salt, for prevention and treatment of mycoplasmosis of animal, both of them may be administered simultaneously to animals, and the acyl peptide (I) or its non-toxic salt may be first administered to animals and then the antibiotics or their non-toxic salt may be administered to the animals in a certain period (generally in a week) after administration of the acyl peptide (I) or its non-toxic salt.

The ratio of the acyl peptide (I) or its non-toxic salt and the antibiotics or their non-toxic salt may vary with the symptoms of the animals infected with mycoplasma, etc, but may usually be 1:10–50 by mol.

The antimycoplasmal agent comprising as an effective ingredient the acyl peptide (I) or its non-toxic salt and the antibiotics or their non-toxic salt may be administered to animals in the same method as described above.

The antimycoplasmal agent of this invention can be administered effectively to all of animals having possibility of infection of mycoplasma, for example, economic domestic animals such a poultry (e.g. chicken turkey, duck, quail, etc.), cattle, pig, sheep, goat, rabbit, mink, dog, cat, mouse, rat and the like.

The antimycoplasmal agent for animal comprising as an effective ingredient the acyl peptide (I) or its non-toxic salt alone, is more improved in the point of being not accompanied with occurrence of antibiotic-resistant microorganisms.

The following Tests and Examples are given to illustrate this invention, but it should be understood that they are not intended to limit this invention.

TEST 1

Materials and Methods

Mycoplasma: *Mycoplasma gallisepticum* 1RF supplied from the National Institute of Animal Health, Ibaraki prefecture, Japan was used.

Chickens used: Broiler males (Chunky), purchased as day-old chickens from a commercial flock free of *Mycoplasma gallisepticum* agglutinins, were maintained under isolation in an electrically heated battery brooder. When birds reached 7 to 8 days of age, they were used for test.

Infection of mycoplasma: *Mycoplasma gallisepticum* 1RF was cultured in PPLO liquid medium (Difco) for 3 to 4 days at 37° C. until the colour of broth changed from red to yellowish organge. An aliquot of the culture ($10^7$–$10^8$ cfu/ml) was used for infection.

Air sac infection were produced by injecting 0.1 ml of the culture into the left posterior air sac of chickens.

Intranasal infections were produced by dropping 0.05 ml of the culture into the nasal cavity of chickens.

Recovery of mycoplasma: Twenty to 21 days after infection, the chickens were killed and recovery of mycoplasma was examined from the trachea, air-sac, and tibia-metatarsus joints.

Recovered organisms were identified as *Mycoplasma gallisepticum* after examining glucose fermentation, colonies, and haemadsorption test.

Inhibition(%) of infection: Average recovery percentage of *Mycoplasma gallisepticum* from trachea, air-sac, and tibia-metatarsus joints was measured infected medicated, and infected non-medicated chickens.

Inhibition(%) was calculated as follows:

$$\text{Inhibition (\%)} = \left(1 - \frac{\text{Average recovery percent of medicated bird}}{\text{Average recovery percent of non-medicated bird}}\right) \times 100$$

10 Chickens (7-day-old) were divided into 2 groups of 5 chickens: group A, *Mycolplasma gallisepticum* 1RF infected and non-medicated; group B, *Mycoplasma gallisepticm* 1RF infected and Compound 3 medicated;

All chickens in group B were injected subcutaneously with Compound 3 (an aqueous solution) in a dose of 0.5 mg per kg of body weight at 7, 8, 9 and 12 days of age, respectively.

At 13 days of age, all chickens in each group were infected by injecting 0.1 ml of the culture ($1.0 \times 10^7$ cfu/ml) of *Mycoplasma gallisepticum* 1RF into the left posterior air sac.

Twenty-one days after infection, all chickens in each group were killed. Recovery of mycoplasma and inhibition(%) of infection were examined.

Results are as follows:

|  |  | Inhibition (%) |
| --- | --- | --- |
| Compound 3 | 0.5 mg/kg/day (group B) | 35 |

TEST 2

Materials and Methods

The same as those of Test 1

20 Chickens (7-day-old) were divided into 4 groups of 5 chickens: group A, *Mycoplasma gallisepticum* 1RF infected and non-medicated, groups B, C, and D, *Mycoplasma gallisepticum* 1RF infected and Compound 1 medicated;

All chickens in groups B, C and D were administered orally with Compound 1 (an aqueous solution) in a dose of 1, 0.1, 0.01 mg per kg of body weight at 7, 8, 9 and 12 days of age, respectively.

At 13 days of age, all chickens in each group were infected by dropping 0.05 ml of the culture ($8.0 \times 10^7$ cfu/ml) of *Mycoplasma gallisepticum* 1RF into the nasal cavity.

Twenty days after infection, all chickens in each group were killed. Recovery of mycoplasma and inhibition(%) of infection were examined.

Results are as follows:

|  | Dose (mg/kg/day) | Inhibition (%) |
| --- | --- | --- |
| Compound 1 | 1 (group B) | 58 |
|  | 0.1 (group C) | 58 |
|  | 0.01 (group D) | 50 |

TEST 3

Materials and Methods

The same as those of Test 1

25 Chickens (8-day-old) were divided into 5 groups of 5 chickens: group A, *Mycoplasma gallisepticum* 1RF infected and non-medicated; groups B, C, D and E, *Mycoplasma gallisepticum* 1RF infected and Compound 1 medicated.

All chickens in groups B, C, D and E were fed continuously with Feed Composition as listed below containing Compound 1 at 40, 10, 2.5 or 0.6 ppm from 7 days before to 20 days after infection.

At 15 days of age, all chickens in each group were infected by dropping 0.05 ml of the culture ($8.0 \times 10^7$ cfu/ml) of *Mycoplasma gallisepticum* 1RF into the nasal cavity.

Twenty days after infection, all chickens in each group were killed. Recovery of mycoplasma and inhibition(%) of infection were examined.

Results are as follows:

|  | Dose (ppm) | Inhibition (%) |
| --- | --- | --- |
| Compound 1 | 40 (group B) | 33 |
|  | 10 (group C) | 78 |
|  | 2.5 (group D) | 44 |
|  | 0.6 (group E) | 33 |

Feed Composition

| Corn | 51.40 (%) |
| --- | --- |
| Milo | 14.00 |
| Soybean meal | 22.00 |
| Fish meal | 8.00 |
| Alfalfa meal | 3.00 |
| Calcium carbonate | 1.50 |
| Tricalcium phosphate | 1.00 |
| Sodium chloride | 0.50 |
| Vitamin A D$_3$ E premix | 0.10 |
| Vitamin B premix*[1] | 0.20 |
| Trace mineral premix*[2] | 0.10 |
| DL-Methionine | 0.20 |
| Compound 1 | 40, 10, 2.5 or 0.6 ppm |

Note:
*[1]Vitamin B premix is composed of vitamin B$_1$, vitamin B$_2$, vitamin B$_6$, vitamin B$_{12}$, biotin, folic acid and calcium pantothenate.
*[2]Trace mineral premix is composed of ferrous sulfate, manganese sulfate, zinc sulfate, copper sulfate, cobalt sulfate and potassium iodide.

TEST 4

Materials and Methods

The same as those of Test 1

15 Chickens (8-day-old) were divided into 3 groups of 5 chickens: group A, *Mycoplasma gallisepticum* infected and non-medicated; groups B and C, *Mycoplasma gallisepticum* 1RF infected and Compound 2 medicated.

All chickens in groups B and C were administered orally with Compound 2 (an aqueous solution) in a dose of 10 or 1 mg per kg of body weight at 8, 9, 12 and 13 days of age, respectively.

At 14 days of age, all chickens in each group were infected by dropping 0.05 ml of the culture ($6.0 \times 10^7$ cfu/ml) of *Mycoplasma gallisepticum* 1RF into the nasal cavity.

Twenty days after infection, all chickens in each group were killed. Recovery of mycoplasma and inhibition(%) of infection were examined.

Results are as follows:

|  | Dose (mg/kg/day) | Inhibition (%) |
| --- | --- | --- |
| Compound 2 | 10 (group B) | 43 |
|  | 1 (group C) | 57 |

TEST 5

Materials and Methods

The same as those of Test 1

20 Chickens (7-day-old) were divided into 4 groups of 5 chickens: group A, *Mycoplasma gallisepticum* 1RF infected and non-medicated; group B, *Mycoplasma gallisepticum* infected and Compound 1 medicated; group C, *Mycoplasma gallisepticum* infected and tylosin medicated; group D, *Mycoplasma gallisepticum* infected and Compound 1+ tylosin medicated.

All chickens in groups B and D were administered orally with Compound (an aqueous solution) 1/in a dose of 1 mg per kg of body weight at 7, 8, 9 and 12 days of age. At 13 days of age, all chickens in each group were infected by dropping 0.05 ml of the culture ($9.0 \times 10^7$ cfu/ml) of *Mycoplasma gallisepticum* 1RF into the nasal cavity.

All chickens in groups C and D were administered orally with tylosin (an aqueous solution) in single dose of 100 mg per kg of body weight at 1 hr after infection.

Twenty days after infection, all chickens in each group were killed. Recovery of mycoplasma and inhibition(%) of infection were examined.

Results are as follows:

|  | Dose (mg/kg/day) | Inhibition (%) |
| --- | --- | --- |
| Compound 1 | 1 (group B) | 50 |
| Tylosin | 100 (group C) | 17 |
| Compound 1 + Tylosin | 1 + 100 (group D) | 100 |

EXAMPLE 1

Compound 1 (1 mg) was dissolved in a distilled water (10 ml). The resultant solution was diluted 10 times with distilled water to give a solution containing Compound 1 (0.01 mg/ml) for oral administration.

EXAMPLE 2

Compound 2 (10 mg) was dissolved in an aqueous solution of 1% sodium bicarbonate (10 ml). The resultant solution was diluted 10 times with distilled water to give a solution containing Compound 2 (0.1 mg/ml) for oral administration.

EXAMPLE 3

Compound 3 (1 mg) was dissolved in a sterile distilled water (10 ml) to give a solution for injection.

EXAMPLE 4

Compound 1 (1 mg) and tylosin (0.1 g) were dissolved in a distilled water (10 ml) to give a solution for oral administration.

We claim:

1. An antimycoplasmal composition for prevention and treatment of mycoplasmosis in animals, which comprises an effective antimycoplasmal amount of an acyl peptide of the formula

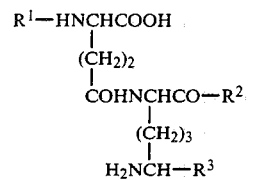

wherein
$R^1$ is lactoyl-alanyl, $R^2$ is carboxymethylamino and $R^3$ is carboxy; or
$R^1$ is heptanoyl, $R^2$ is 1-carboxyethylamino and $R^3$ is carboxy; or
$R^1$ is stearoyl, $R^2$ is 1-carboxyethylamino and $R^3$ is hydrogen.
or its non-toxic salt, and an antibiotic selected from the group consisting of tylosin, tetracyclines, chloramphenicol, tiamulin and spectinomycin, wherein the ratio of the acyl peptide or its non-toxic salt and the antibiotic is 1:10–50 by mol.

2. The antimycoplasmal composition according to claim 1, wherein the antibiotic is tylosin.

3. A method for prevention and treatment of mycoplasmosis in animals which comprises orally administering to the animal a composition comprising an effective antimycoplasmal amount of an acyl peptide of the formula

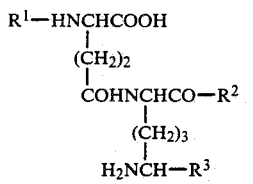

wherein
$R^1$ is lactoyl-alanyl, $R^2$ is carboxymethylamino and $R^3$ is carboxy; or
$R^1$ is heptanoyl, $R^2$ is 1-carboxyethylamino and $R^3$ is carboxy; or
$R^1$ is stearoyl, $R^2$ is 1-carboxyethylamino and $R^3$ is hydrogen,
or its non-toxic salt, and an antibiotic selected from the group consisting of tylosin, tetracyclines, chloramphenicol, tiamulin and spectinomycin, wherein the ratio of the acyl peptide or its non-toxic salt and the antibiotic is 1:10–50 by mol.

4. The method according to claim 3 wherein the amount of the acyl peptide or its non-toxic salt is 0.01–10 mg/kg/day.

5. The method according to claim 3, wherein the animals are poultry.

6. The method according to claim 11, wherein the poultry is chicken.

* * * * *